(12) United States Patent
Nakajima et al.

(10) Patent No.: US 9,011,396 B2
(45) Date of Patent: Apr. 21, 2015

(54) DISPOSABLE WEARING ARTICLE WITH MOVEABLE SKIN-CONTACTABLE SHEET

(75) Inventors: Kaiyo Nakajima, Kanonji (JP); Haruki Toda, Kanonji (JP); Yoshikazu Tanaka, Kanonji (JP)

(73) Assignee: Unicharm Corporation, Ehime (JP)

( * ) Notice: Subject to any disclaimer, the term of this patent is extended or adjusted under 35 U.S.C. 154(b) by 279 days.

(21) Appl. No.: 13/578,843

(22) PCT Filed: Feb. 17, 2011

(86) PCT No.: PCT/JP2011/053411
§ 371 (c)(1),
(2), (4) Date: Aug. 14, 2012

(87) PCT Pub. No.: WO2011/102427
PCT Pub. Date: Aug. 25, 2011

(65) Prior Publication Data
US 2012/0311770 A1 Dec. 13, 2012

(30) Foreign Application Priority Data
Feb. 19, 2010 (JP) ................................. 2010-035253

(51) Int. Cl.
*A61F 13/15* (2006.01)
*A61F 13/49* (2006.01)
(Continued)

(52) U.S. Cl.
CPC ..... *A61F 13/49011* (2013.01); *A61F 13/49466* (2013.01); *A61F 13/5116* (2013.01); *A61F 13/513* (2013.01); *A61F 2013/00404* (2013.01); *A61F 2013/15024* (2013.01);
(Continued)

(58) Field of Classification Search
CPC .................... A61F 13/49019; A61F 13/51104; A61F 13/51108; A61F 2013/51316; A61F 2013/51361
USPC .............. 604/385.01, 385.101, 386, 397, 398
See application file for complete search history.

(56) References Cited

U.S. PATENT DOCUMENTS 1,931,357 A * 10/1933 Potwin .......................... 604/399
3,756,878 A * 9/1973 Willot .............................. 156/70
(Continued)

FOREIGN PATENT DOCUMENTS

| JP | 10033589 A | 2/1998 |
|---|---|---|
| JP | 2002272766 A | 9/2002 |

(Continued)

OTHER PUBLICATIONS

International Search Report and Written Opinion for PCT/JP2011/053411, dated Apr. 19, 2011.

*Primary Examiner* — Tan-Uyen T. Ho
*Assistant Examiner* — Kathryn E Ditmer
(74) *Attorney, Agent, or Firm* — Lowe Hauptman & Ham, LLP

(57) ABSTRACT

A disposable wearing article has a skin-contactable sheet moveable relative to a chassis. The chassis includes an inner sheet, an outer sheet and a liquid-absorbent panel interposed between these inner and outer sheets. The absorbent panel lies at least in the crotch region and extends into the front and rear waist regions in the longitudinal direction. In the rear waist region, a skin-contactable sheet adapted to come in contact with the wearer's skin is attached to the inner surface of the inner sheet. The skin-contactable sheet has front and rear ends extending in the transverse direction and lateral portions extending in the longitudinal direction and only the lateral portions are bonded to the inner sheet.

14 Claims, 14 Drawing Sheets

(51) Int. Cl.
*A61F 13/511* (2006.01)
*A61F 13/74* (2006.01)
*A61F 13/76* (2006.01)
*A61F 13/494* (2006.01)
*A61F 13/513* (2006.01)
*A61F 13/00* (2006.01)

(52) U.S. Cl.
CPC ............... *A61F 2013/15154* (2013.01); *A61F 2013/51182* (2013.01); *A61F 2013/51316* (2013.01)

(56) References Cited

U.S. PATENT DOCUMENTS

| | | | |
|---|---|---|---|
| 5,531,730 A | 7/1996 | Dreier | |
| 5,540,671 A | 7/1996 | Dreier | |
| 6,648,868 B2 * | 11/2003 | Sayama et al. | 604/385.22 |
| 2002/0138058 A1 | 9/2002 | Mishima et al. | |
| 2002/0147438 A1 * | 10/2002 | Tanaka et al. | 604/392 |
| 2005/0038401 A1 * | 2/2005 | Suzuki et al. | 604/385.01 |
| 2005/0165375 A1 * | 7/2005 | Fernfors et al. | 604/378 |
| 2006/0270302 A1 * | 11/2006 | Ando et al. | 442/328 |
| 2007/0239132 A1 * | 10/2007 | Mishima | 604/385.101 |
| 2008/0114321 A1 * | 5/2008 | Otsubo | 604/385.01 |

FOREIGN PATENT DOCUMENTS

| | | |
|---|---|---|
| JP | 3457003 B2 | 10/2003 |
| JP | 3493211 B2 | 2/2004 |

* cited by examiner

DISPOSABLE WEARING ARTICLE WITH MOVEABLE SKIN-CONTACTABLE SHEET

RELATED APPLICATIONS

The present application is a National Phase of International Application Number PCT/JP2011/053411, filed Feb. 17, 2011, and claims priority from Japanese Application Number 2010-035253, filed Feb. 19, 2010.

TECHNICAL FIELD

The present invention relates to disposable wearing articles and more specifically to disposable wearing articles such as disposable urine absorbent pads, disposable diapers, disposable toilet-training pants, disposable incontinent pants and disposable sanitary pants.

BACKGROUND

Conventionally, in disposable diapers having front and rear waist regions and a crotch region extending between the front and rear waist regions, it is known that the diaper includes inner and outer sheets, an absorbent core interposed between the inner and outer sheets and a separate sheet attached to a skin-facing side of the inner sheet facing the wearer's body. For example, JP 3493211 B2 (PTL 1) discloses a diaper further including a barrier sheet layered on the inner sheet. JP 3457003 B2 (PTL 2) discloses a diaper in which a inner sheet is formed with sheet-like pocket cuffs.

In the diapers disclosed in PTL 1 and PTL 2, the separate sheet layered on the inner sheet extends in a transverse direction of the diaper and is bonded along lateral portions and at least one of front and rear ends intersecting with the lateral portions of the separate sheet to the inner sheet.

CITATION LIST

Patent Literature

PTL 1: JP 3493211 B2
PTL 2: JP 3457003 B2

SUMMARY

Technical Problem

In both the diapers disclosed in PTL 1 and PTL 2, the separate sheet layered on the inner sheet is bonded to the inner sheet not only along the lateral portions but also along at least one of the front and rear ends thereof. As a result, it is impossible for this separate sheet to move in the longitudinal direction or the transverse direction relative to the inner sheet as if this separate sheet and the inner sheet pass each other.

An object of the present invention is to provide a disposable wearing article improved so that a skin-contactable sheet lying on a skin-facing side of a chassis may be movable in a longitudinal direction and/or transverse direction relative to the chassis.

Solution to Problem

This invention relates to a disposable wearing article having a longitudinal direction and a transverse direction and including:

a chassis including a skin-facing side, a non-skin-facing side opposite to the skin-facing side, front waist region, a rear waist region and a crotch region continuously extending between the front and rear waist regions in the longitudinal direction, lateral portions extending in the longitudinal direction and front and rear ends extending in the transverse direction; and a skin-contactable sheet lying on the skin-facing side of the chassis.

According to the present invention, the skin-contactable sheet extends in the transverse direction and lies at least in the rear waist region and joined to the chassis only along the lateral portions of the skin-contactable sheet.

According to one embodiment of this invention, the skin-contactable sheet is elastically contractible at least in the transverse direction.

According to another embodiment of this invention, the skin-contactable sheet has a plurality of ridges extending in the longitudinal direction and grooves each formed between each pair of the adjacent ridges.

According to still another embodiment of this invention, the skin-contactable sheet has front and rear ends extending in the transverse direction and a notch region defined by partially cutting out the front end.

According to further another embodiment of this invention, the two or more skin-contactable sheets are arranged in the longitudinal direction.

According to yet another embodiment of this invention, in an overlapping region of the skin-contactable sheet and the chassis, at least one of a side of the skin-contactable sheet facing the chassis and a side of the chassis facing the skin-contactable sheet is formed with friction resistance alleviating means.

According to one alternative embodiment of this invention, the friction resistance alleviating means is formed of lubricant material.

According to another alternative embodiment of this invention, the lubricant material is silicon resin.

According to still another alternative embodiment of this invention, a dimension of the crotch region in the transverse direction is smaller than those of the front and rear waist regions.

According to further another alternative embodiment of this invention, a dimension of the rear waist region in the longitudinal direction is larger than that of the front waist region.

According to yet another alternative embodiment of this invention, the chassis is formed on the skin-facing side with a pair of leakage-barrier cuffs including:

bonded regions extending along the lateral portions of the wearing article in the longitudinal direction and bonded to the chassis; and free regions not bonded to the chassis and adapted to be spaced therefrom, wherein the skin-contactable sheet is attached to the chassis so as to at least partially overlap with the leakage-barrier cuffs.

According to one additional embodiment of this invention, the skin-contactable sheet is attached so as to be interposed between the leakage-barrier cuffs and the chassis.

According to another additional embodiment of this invention, the skin-contactable sheet is elastically stretchable and contractible in the transverse direction in a region of the skin-contactable sheet overlapping the leakage-barrier cuffs.

Advantageous Effects of Invention

According to one or more embodiments of this invention, the skin-contactable sheet lying on the skin-facing side of the chassis is bonded to the chassis only along the lateral portions of the skin-contactable sheet and the non-bonded regions other than the lateral portions may move relative to the chassis. The skin-contactable sheet relative to the chassis may conform to movements of the wearer's body and the wearing article should not sensitively rub the wearer's skin. In consequence, undesirable irritation to the wearer's skin may be alleviated.

DESCRIPTION OF EMBODIMENTS

Figure 1:
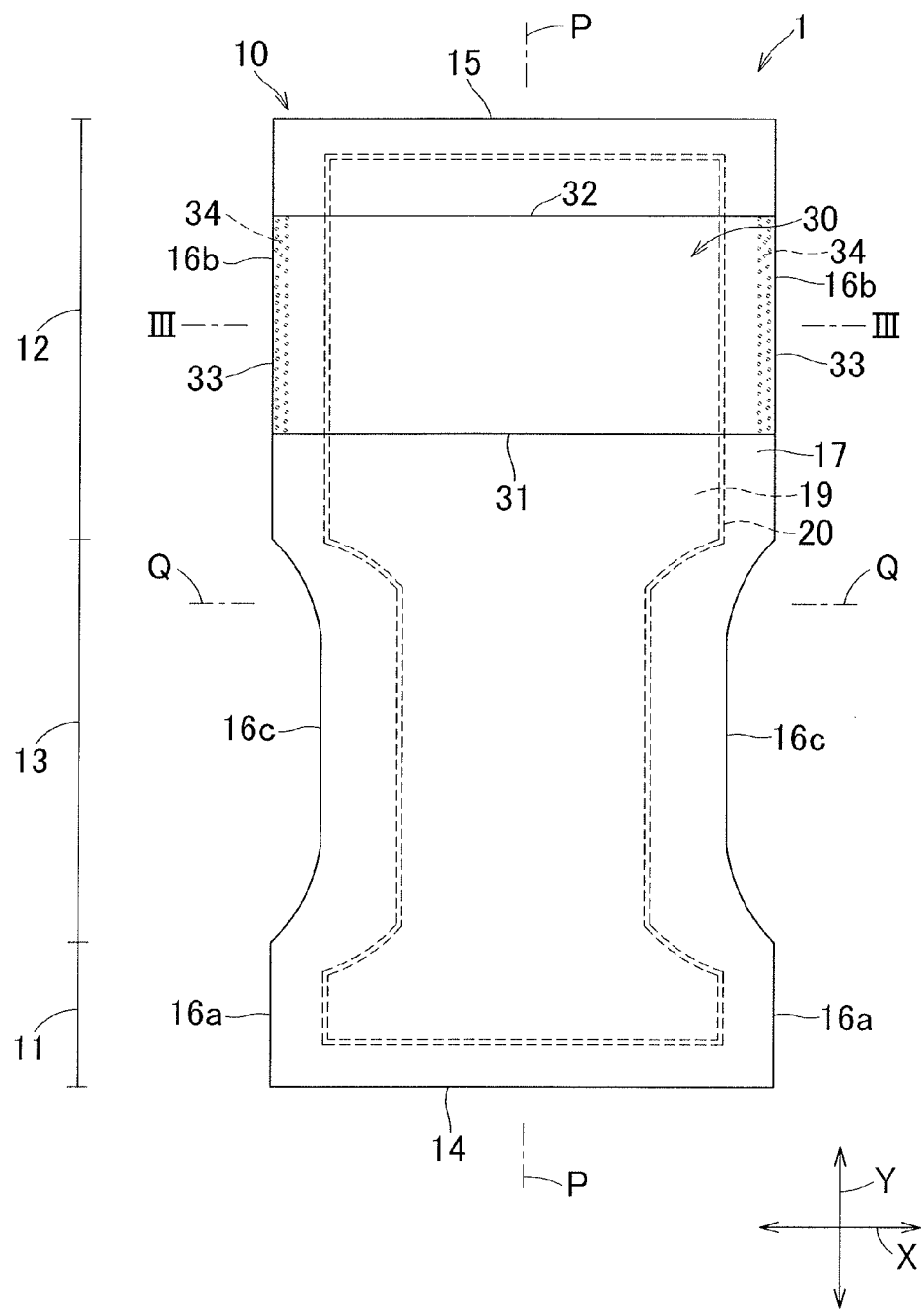
FIG. 1 is a plan view of a disposable urine absorbent pad as one example of disposable wearing articles according to a first embodiment of this invention.
Figure 2:
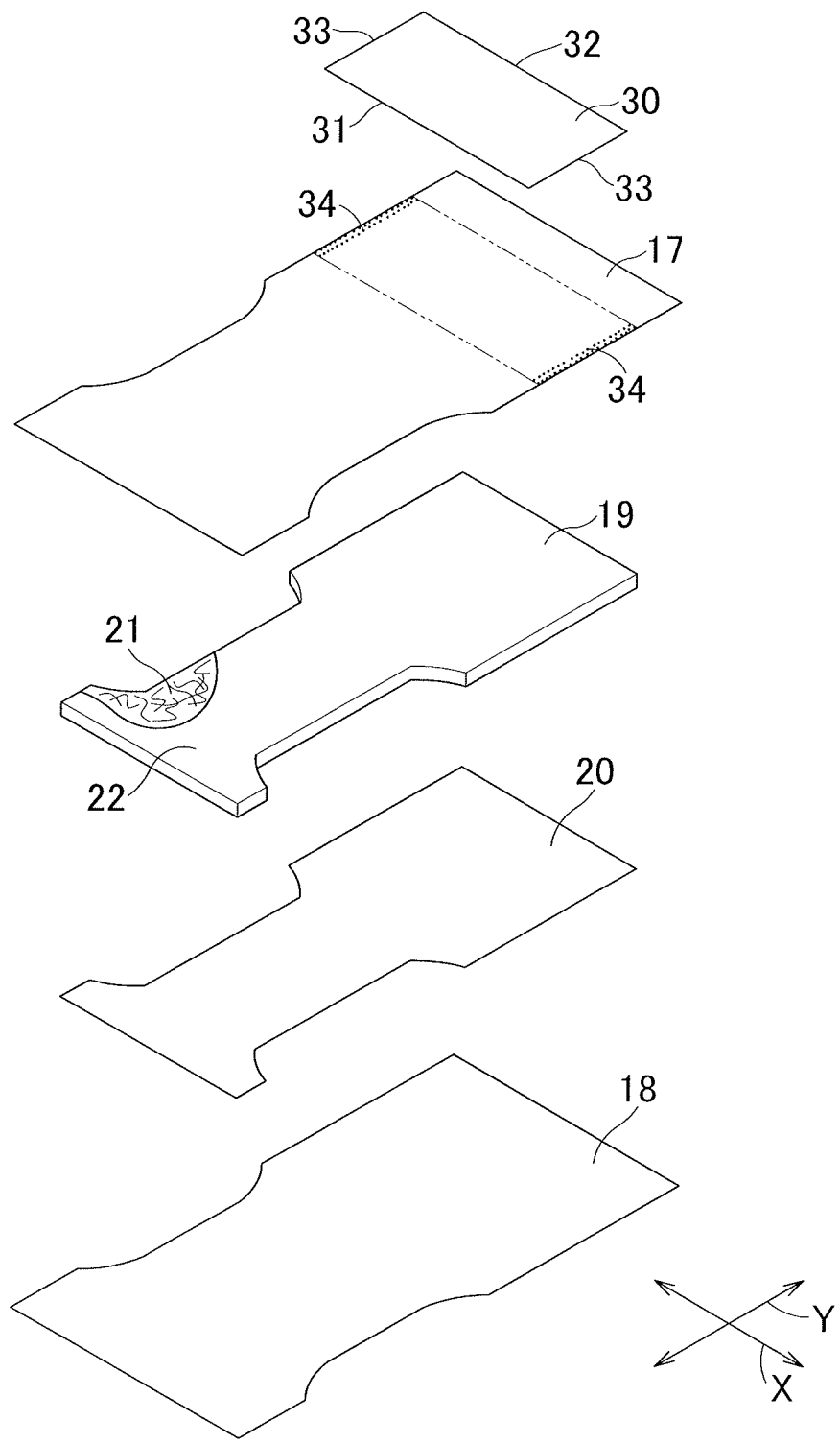
FIG. 2 is an exploded diagram corresponding to FIG. 1.
Figure 3:
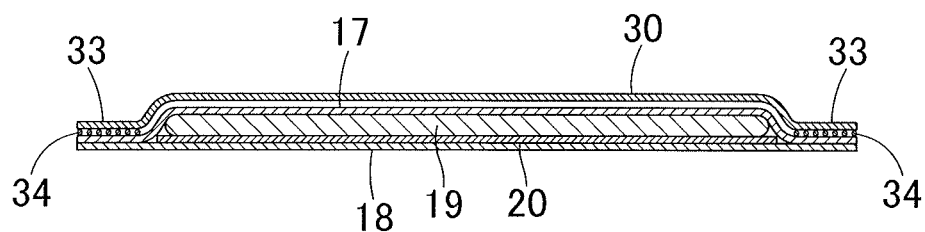
FIG. 3 is a sectional view taken along line III-III in FIG. 1.
Figure 4:
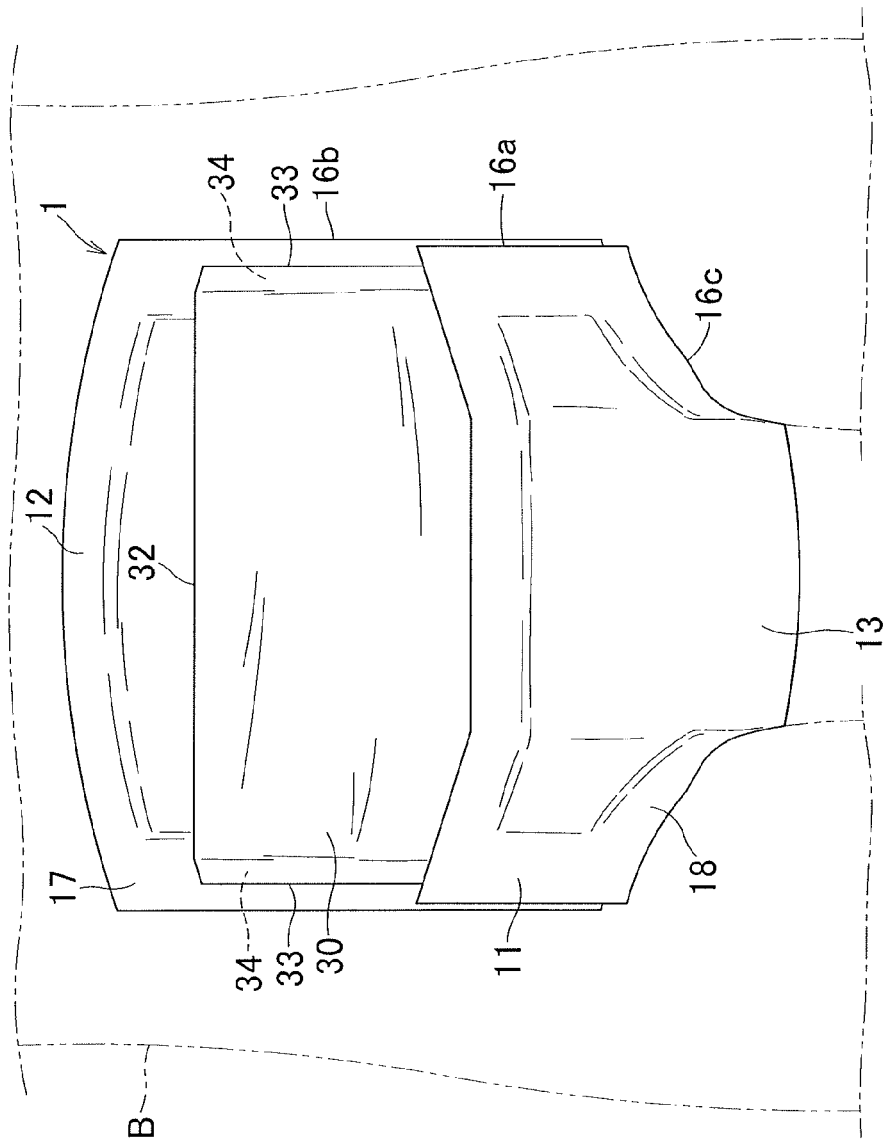
FIG. 4 is a diagram illustrating the pad in a worn state.
Figure 5:
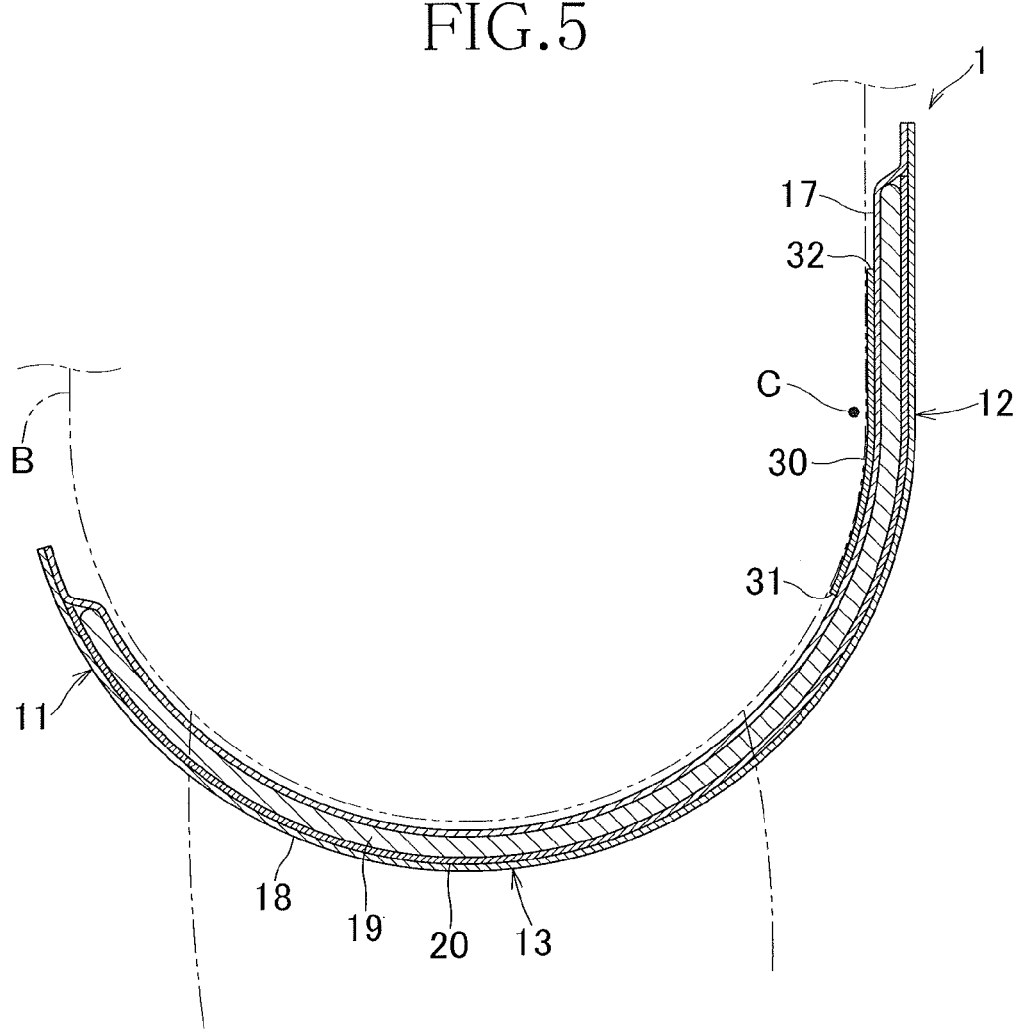
FIG. 5 is a diagram illustrating the pad in a worn state.
Figure 6:
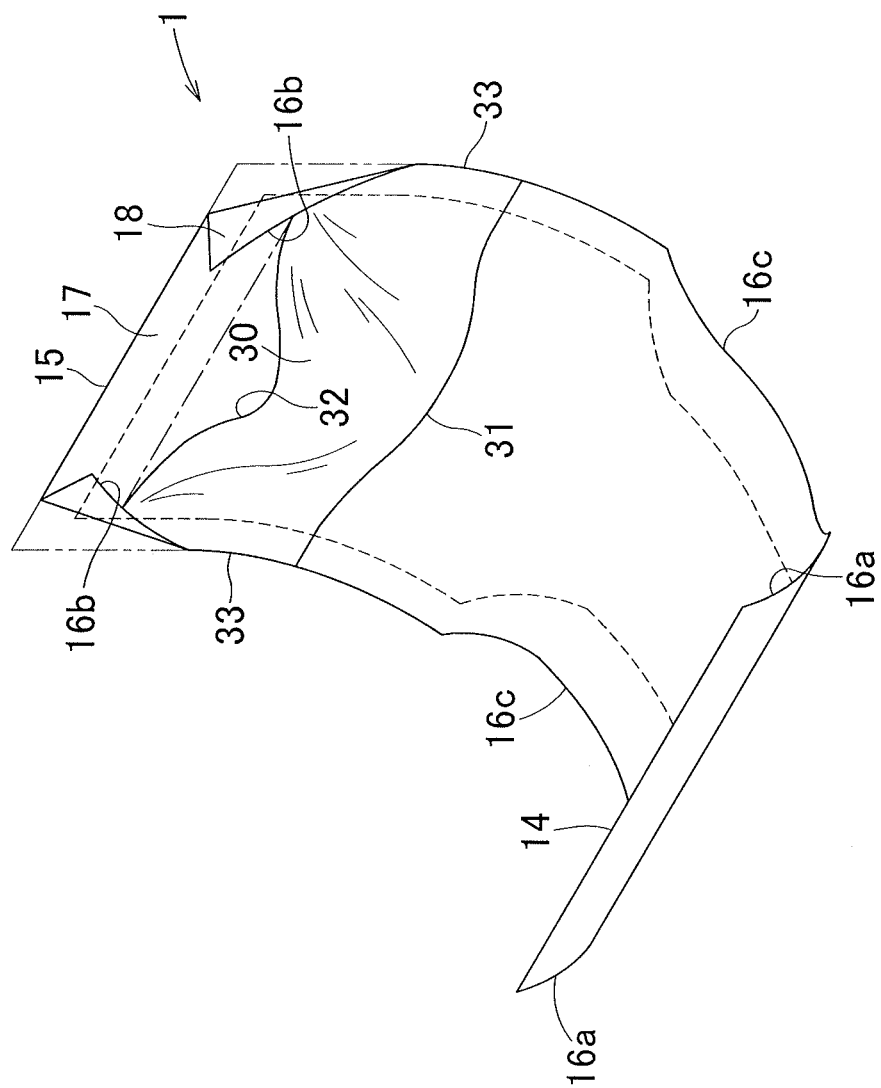
FIG. 6 is a diagram illustrating the pad in a worn state.

<First Embodiment>
FIG. 1 is a plan view of a disposable urine absorbent pad 1 as one example of disposable wearing articles according to this invention. FIG. 2 is a partially cutaway exploded diagram of the pad 1. FIG. 3 is a sectional view taken along line in FIG. 1. FIGS. 4 and 5 show the pad 1 in a worn state. FIG. 6 is a diagram illustrating the pad 1 in a worn state. The pad 1 has an imaginary longitudinal center line P-P bisecting a dimension in the transverse direction X and an imaginary transverse center line Q-Q bisecting a dimension in the longitudinal direction Y wherein the pad 1 is substantially symmetric about the imaginary longitudinal center line P-P. In the accompanying drawings, one of each pair of symmetrically arranged components was not designated by reference sign or numeral as the case may be.
The pad 1 includes a chassis 10 including a skin-facing side facing the wearer's body, a garment-facing side opposite to the skin-facing side, a front waist region 11, a rear waist region 12 and a crotch region 13 extending between the front and rear waist regions 11, 12, and a skin-contactable sheet 30 attached to the skin-facing side of the chassis 10.
The chassis 10 includes front and rear ends 14, 15 extending in the transverse direction X so as to be opposed to each other about the imaginary transverse center line Q-Q and lateral portions extending in the longitudinal direction Y so as to be opposed to each other about the imaginary longitudinal center line P-P. The lateral margins include front lateral portions 16a located in the front waist region 11, the rear lateral portions 16b located in the rear waist region 12 and crotch lateral portions 16c located in the crotch region 13. Both the front and rear lateral portions 16a, 16b extend substantially in parallel to the imaginary longitudinal center line P-P and the crotch lateral portions 16c are concavely curved so that these lateral portions may come in contact along the wearer's thighs with good fit during use of the pad 1. The crotch region 13 is defined by such crotch lateral portions 16c. According to this embodiment, a large portion of the crotch region 13 extends forward from the imaginary transverse center line Q-Q in the longitudinal direction Y and a dimension of the rear waist region 12 in the longitudinal direction Y is larger than that of the front waist region 11.

The chassis 10 includes an inner sheet 17 defining a skin-facing side, an outer sheet 18 opposite to the inner sheet 17 and defining a garment-facing side and a liquid-absorbent panel 19 interposed between the inner and outer sheets 17, 18. A leakage-barrier sheet 20 is interposed between the outer sheet 18 and the absorbent panel 19 so as to cover a bottom surface of the absorbent panel 19. The inner sheet 17 and the absorbent panel 19, the absorbent panel 19 and the leakage-barrier sheet 20, and the leakage-barrier film and the outer sheet 18 are respectively bonded to each other with hot melt adhesives in an intermittent pattern.

As material of the inner and outer sheets 17, 18, at least one of a spun bonded fibrous nonwoven fabric, a spun bonded/melt blown/spun bonded (SMS) fibrous nonwoven fabric and an air-through fibrous nonwoven fabric or the like may be used. As material of the leakage-barrier sheet 20, a moisture-pervious and liquid-impervious plastic film may be used. The absorbent panel 19 may be formed of a liquid-absorbent core 21 composed of a mixture of fluff pulp and superabsorbent polymer particles compressed and molded and a liquid-diffusion sheet 22 wrapping such a core.

The absorbent panel 19 extends across at least the crotch region 13 and further extends into the front and rear waist regions 11, 12 in the longitudinal direction Y. The absorbent panel 19 has a dimension in the transverse direction X reduced in the crotch region 13 and has a shape constricting toward the imaginary transverse center line Q-Q.

In the rear waist region 12, a skin-contactable sheet 30 adapted to come in contact with the wearer's skin is attached to an inner side of the inner sheet 17. More specifically, the skin-contactable sheet 30 has front and rear ends 31, 32 extending in the transverse direction X, lateral portions 33 extending in the longitudinal direction Y. The skin-contactable sheet 30 extends between one of the rear lateral portions 16b and is bonded at the lateral portions 33 to the inner sheet 17 by bonding means 34 such as hot melt adhesives. In other words, between the pair of the bonding means 34, the skin-contactable sheet 30 and the inner sheet 17 are not bonded to each other. As material of such a skin-contactable sheet 30, for example, a spun bonded fibrous nonwoven fabric, an SMS fibrous nonwoven fabric or the like which provides the wearer's skin with frictional irritation as mild as possible may be used.

FIGS. 4 and 5 illustrate the pad 1 in the configuration it would assume when placed on a wearer, wherein the wearer B is indicated by imaginary lines. As illustrated, the crotch region 13 is placed on the wearer's crotch, the front waist region 11 is placed on the wearer's ventral side and the rear waist region 12 is placed on the wearer's dorsal side. Generally, the pad 1 is used in a manner such that the pad 1 is covered with the diaper or the diaper cover in order to keep the pad 1 in close contact with the wearer. In this regard, referring to FIGS. 4 and 5, such a diaper or a diaper cover is omitted for convenience of illustration. According to this embodiment, the front lateral portions 16a and the rear lateral portions 16b of the pad 1 are not brought in contact with each other but spaced apart from each other between the wearer's ventral side and the wearer's dorsal side.

In the pad 1, the rear waist region 12 is dimensioned to be larger than that of the front waist region 11 in the longitudinal direction Y and, in consequence, the wearer's dorsal side may be covered with the pad 1 over a sufficiently large area. Referring to FIG. 5, a sacral bone region C of the wearer B is covered with the pad 1 in the rear waist region 12. The pad 1 is configured to be readily put on and put off and suitable for the wearer who is obliged to lie on a bed for most of a day. Particularly when the wearer is lying on the back, urine discharged by the wearer flows toward the dorsal side and such urine flowing toward the dorsal side may be reliably absorbed by configuring the dimension of the rear waist region 12 in the longitudinal direction Y to be relatively large. When the wearer lie on the back for a long period, the sacral bone region projecting relative to the remaining region might be pressed by its own weight against the bed or any accessories thereof and cause bedsores. However, by configuring the pad 1 to be positioned between the sacral bone and the bed, the pad 1 may function as a cushion to alleviate such a problem.

The skin-contactable sheet 30 is bonded to the inner sheet 17 only along the lateral portions 33 of the sheet 30 and therefore the skin-contactable sheet 30 may be spaced apart from the inner sheet 17 in a region defined between the pair of bonding means 34 in the transverse direction X, so that the skin-contactable sheet 30 is movable relative to the inner sheet 17.

With the pad 1 in a worn state, the skin-contactable sheet 30 is located on the dorsal side of the wearer B, preferably so as to cover the sacral bone region C. In this state, if the wearer sits up, for example, by reclining the bed, the buttocks may move forward due to the wearer's body weight. Even if such a movement of the buttocks occur, the skin-contactable sheet 30 and the inner sheet 17 may relatively move in the longitudinal direction Y as if these two sheets pass each other and, consequently the skin-contactable sheet 30 may conform to the wearer B.

FIG. 6 exemplarily illustrates the skin-contactable sheet 30 which has moved relative to the inner sheet 17 as if these two sheets pass each other. When the skin-contactable sheet 30 moves with the wearer's movements, the skin-contactable sheet 30 may deform so that a central region of the skin-contactable sheet 30 as viewed in the transverse direction sags downward in the longitudinal direction Y. Sagging of the skin-contactable sheet 30 allows the rear lateral portions 16b of the chassis 10 to be pulled and thereby to be deformed. The reason why the chassis 10 is deformable as described above is that this pad 1 is adapted to be put on the wearer's body by the intermediary of a separately prepared diaper cover and not adapted to be put in close contact with the wearer's body by joining the front lateral portions 16a to the rear lateral portions 16b.

As has been described just above, the skin-contactable sheet 30 conforms to movements of the wearer's body and sensitive friction might occur between the wearer's dorsal side and the skin-contactable sheet 30. In consequence, undesirable skin irritation due to the friction may be alleviated. In addition, the skin-contactable sheet 30 is located to cover the sacral bone region which is adapted to develop the bedsores and, in consequence, it is possible to prevent development of bedsores and worsening thereof due to the friction between the wearer's dorsal region and the skin-contactable sheet 30.

While the dimension in the transverse direction X of the skin-contactable sheet 30 is substantially the same as that of the inner sheet 17 according to this invention, the dimension of the skin-contactable sheet 30 may be larger than that of the inner sheet 17 and the skin-contactable sheet 30 may be folded along opposite fold lines extending in the longitudinal direction Y in actual use. The dimension in the transverse direction X of the skin-contactable sheet 30 may be relatively large in this manner to enlarge a relative movement of the skin-contactable sheet 30 to the inner sheet 17 so that the skin-contactable sheet 30 may be moved relative to the inner sheet 17 without pulling the rear lateral portions 16b of the chassis 10. Furthermore, the alternative dimension as has been described above allows the skin-contactable sheet 30 to move not only in the longitudinal direction Y but also in the transverse direction X and, for example, even when the wearer turns over in bed, any sensitive friction between the chassis 10 and the wearer's skin may be prevented.

<Second Embodiment>

Figure 7:
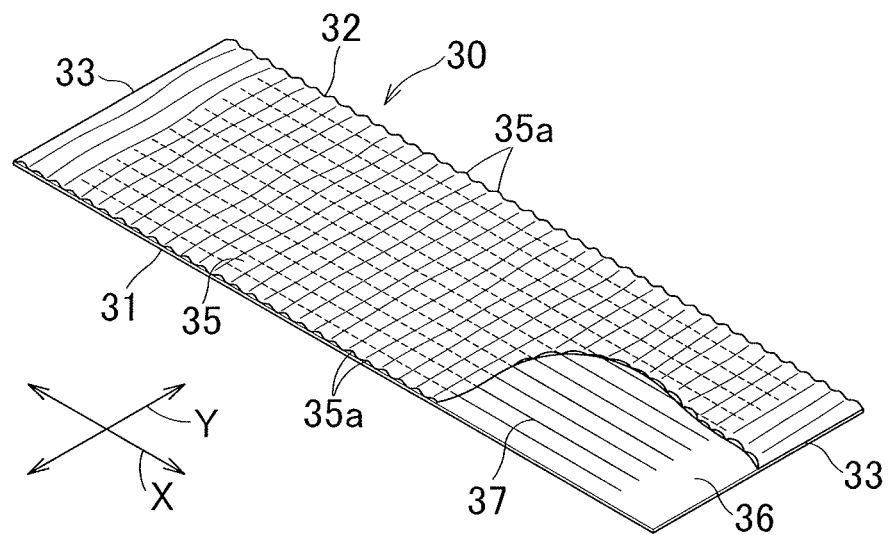
FIG. 7 is a perspective view of a skin-contactable sheet according to a second embodiment.
Figure 8:
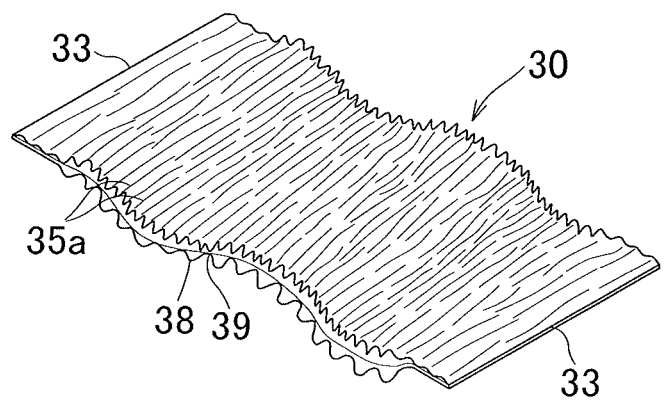
FIG. 8 is a diagram illustrating the skin-contactable sheet of FIG. 7 in a state of contraction.
Figure 9:
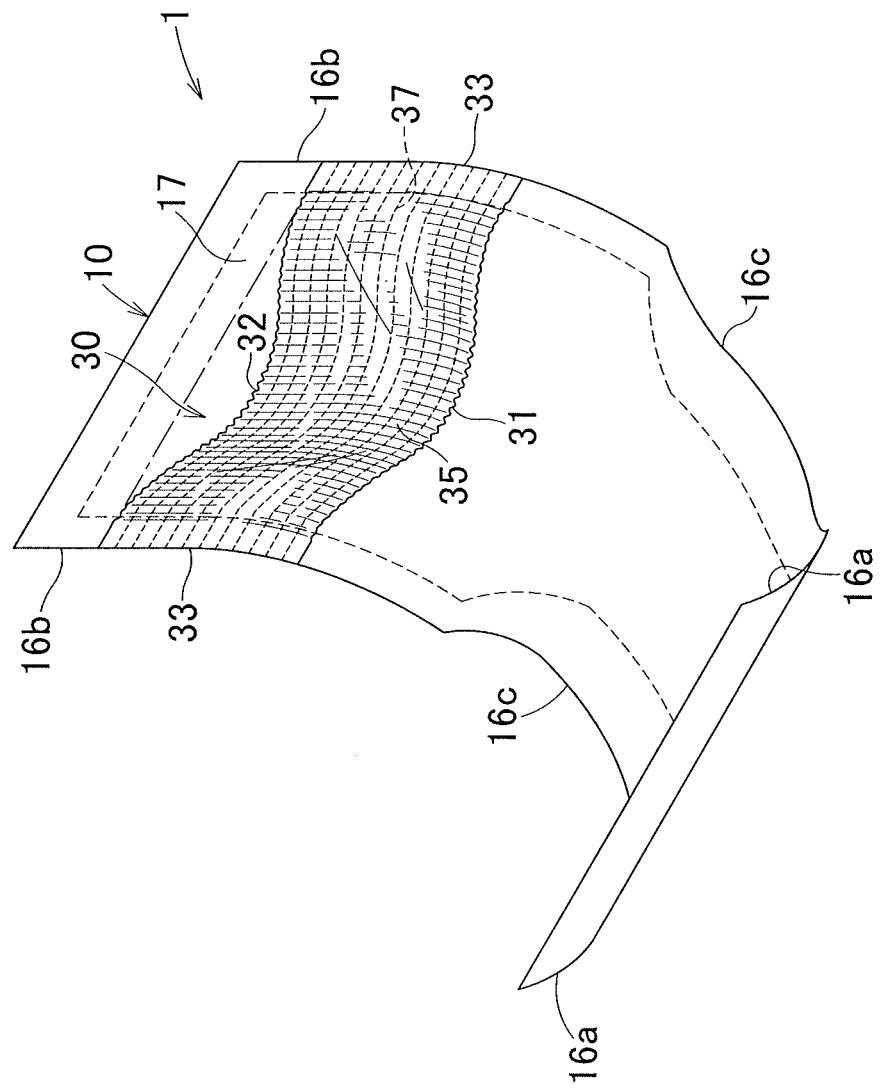
FIG. 9 is a diagram similar to FIG. 6, illustrating the pad in a worn state.

FIGS. 7 and 8 illustrate the skin-contactable sheet 30 used in the pad 1 according to a second embodiment. FIG. 9 is a diagram similar to FIG. 6 for the first embodiment, illustrating the shape during use of the pad 1. According to this second embodiment, the skin-contactable sheet 30 has a constitution different from that according to the first embodiment. The components similar to those in the first embodiment are designated by the reference signs used in the first embodiment and details of such components will not be repetitively described.

The skin-contactable sheet 30 includes a first sheet 35 lying on the skin-facing side, a second sheet 36 opposed the first sheet 35 and lying on the side of the inner sheet 17 and a plurality of elastic elements 37 interposed between the first and second sheets 35, 36. As material of the first sheet 35, a fibrous nonwoven fabric formed on the skin-facing side thereof with a plurality of ridges 35a extending in the longitudinal direction Y. For example, a fibrous web constituting the first sheet 35 may be continuously subjected to air jets from an array of nozzles arranged above the fibrous web to form the fibrous web in regions thereof directly subjected to the air jets with grooves and in regions thereof not directly subjected to the air jets with the ridges 35a. A pitch defined by a dimension between each pair of the adjacent ridges 35a may be, for example, in a range of about 3 mm to about 6 mm. In such a first sheet 35, the constituent fibers of the fibrous web may be reoriented or rearranged to control the fiber density in the grooves defined between the adjacent ridges 35a to be lower than that in the ridges 35a. Besides, amount of the air ejected to the fibrous web may be intermittently increased to form the grooves with apertures intermittently formed in the longitudinal direction Y. Alternatively, the first sheet may be subjected to water jet processing, steam jet processing, press working or gear working to form the ridges.

As the second sheet 36, an ordinary fibrous nonwoven fabric having no ridge may be used. The elastic elements 37 extend in the transverse direction X so as to be spaced apart from each other in the longitudinal direction Y and are contractibly attached to the skin-contactable sheet 30 under tension. The elastic elements 37 attached in this manner do not extend to the lateral portions 33 of the skin-contactable sheet 30, more specifically, the respective ends of the elastic elements 37 are spaced apart inwardly from the lateral portions 33.

FIG. 8 illustrates the skin-contactable sheet 30 in which the elastic elements 37 are in a state of contraction. Referring to the first sheet 35, the adjacent ridges 35a come closer to each other in the transverse direction X and, in the second sheet 36, a plurality of ridges 38 and a plurality of grooves 39 both extending in the longitudinal direction Y are formed due to contraction of the elastic elements 37. The ridges 39 project toward the inner sheet 17 and the grooves 39 are defined between each pair of the adjacent ridges 38.

Being free from the presence of the elastic elements 37, the lateral portions 33 of the skin-contactable sheet 30 remain in a flat state without being formed with the ridges 38 and the grooves 39. These flat lateral portions 33 are coated with bonding means such as hot melt adhesive to bond the skin-contactable sheet 30 to the inner sheet 17. Assuming that the skin-contactable sheet 30 is bonded to the inner sheet 17 in the region formed with the ridges 38 and the grooves 39, there is a possibility that the bonding strength might be deteriorated. Such deterioration of the bonding strength can be avoided by bonding the skin-contactable sheet 30 to the inner sheet 17 along the opposite flat lateral margins 33.

The elastic elements 37 may be attached to the skin-contactable sheet 30 to make the skin-contactable sheet 30 elastically contractible in the transverse direction X. Referring to FIG. 8, such skin-contactable sheet 30 is attached to the inner sheet 17 in a contracted state.

FIG. 9 illustrates the skin-contactable sheet 30 bonded to the chassis 10 and having moved in the longitudinal direction Y relative to the chassis 10 upon putting it on the wearer's body. More specifically, when the skin-contactable sheet 30 put in contact with the wearer's dorsal region moves with movements of the wearer's dorsal region, the elastically contractible skin-contactable sheet 30 may stretchably move relative to the inner sheet 17. In consequence, the rear lateral portions 16b of the chassis 10 might be pulled and deformed due to the movements of the wearer's dorsal region.

The second sheet 36 of the skin-contactable sheet 30 is formed with the ridges 38 and the grooves 39 developed under contraction of the elastic elements 37 and consequently the area in which the second sheet 36 is put in contact with the inner sheet 17 may be reduced. By reducing the contact area in this manner, it is possible to alleviate a frictional resistance between these two sheets and thereby facilitate the skin-contactable sheet 30 to move relative to the inner sheet 17.

The first sheet 35 is formed on the side thereof facing the wearer's body with the plurality of ridges 35a making it possible to reduce an area over which the first sheet 35 comes in contact with the wearer's skin and thereby alleviate a skin irritation. In addition, an interval between each pair of the adjacent ridges 35a is reduced upon contraction of the elastic elements 37 and, in consequence, flexibility of the first sheet 35 as a whole may be improved. When a hot melt adhesive is used to bond the first sheet 35, the second sheet 36 and the elastic elements 37 together, a stiffness in bonded zones might become relatively high. However, areas actually coming in contact with the wearer's skin are limited to the ridges 35a of the first sheet 35 and therefore the wearer's skin should not be irritated by the high stiffness area.

While the elastic elements 37 are attached between the first and second sheets 35, 36 to obtain the skin-contactable sheet 30 adapted to be elastically contractible in the transverse direction X according to this embodiment, it is possible to adopt the skin-contactable sheet 30 formed of an elastic fibrous nonwoven fabric including elastic fibers. In this regard, such an elastic fibrous nonwoven fabric will be not necessarily formed with the ridges 38 and the grooves 39. Furthermore, it is also possible, for example, to contractibly attach under tension separately prepared elastic elements extending in the longitudinal direction Y to the skin-contactable sheet 30 so that the skin-contactable sheet 30 may be elastically contractible also in the longitudinal direction Y or to configure part of the elastic elements extending in the transverse direction X to be convex in the longitudinal direction Y so that the elastic elements 37 may be attached as a whole in a curved state. As material of the elastic elements 37, various kinds of known materials usually used in the relevant technical field may be used without limitation. For example, while the thread, string or strand elastic elements 37 are used in the illustrated embodiment, it is possible to use ribbon- or tape-like elastic elements each having a width dimension larger than each of the thread, string or strand elastic elements. As material of the thread, string or strand elastic elements, natural or synthetic rubber may be used and as material of the ribbon- or tape-like elastic elements, at least one of polyurethane and an elastic fibrous nonwoven fabric may be used. While the fibrous nonwoven fabric formed with the ridges 35a is used as the first sheet 35 in this embodiment, it is also possible to use a flat fibrous nonwoven fabric not formed with the ridges 35a.

<Third Embodiment>

Figure 10:
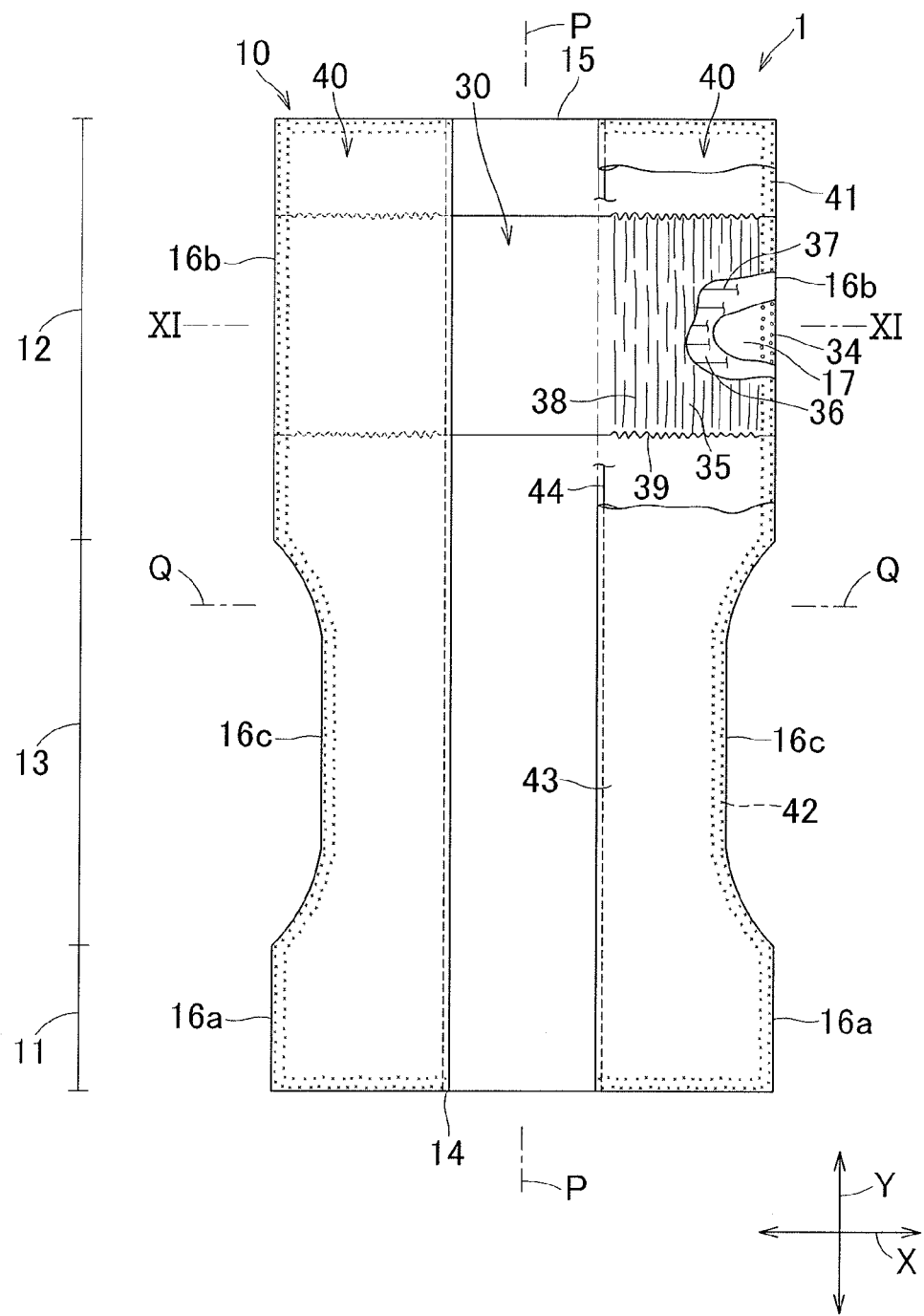
FIG. 10 is a partially cutaway plan view of the pad according to a third embodiment.
Figure 11:
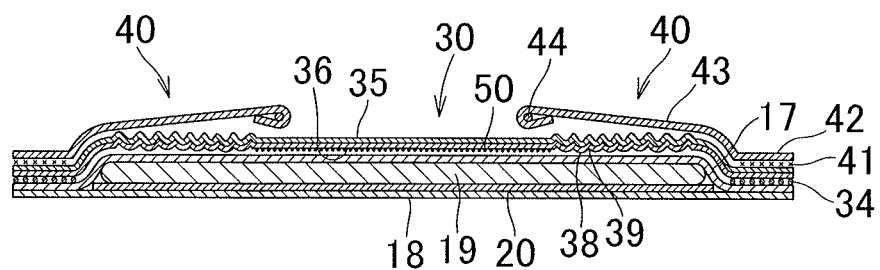
FIG. 11 is a sectional view taken along a line XI-XI in FIG. 10.
Figure 12:
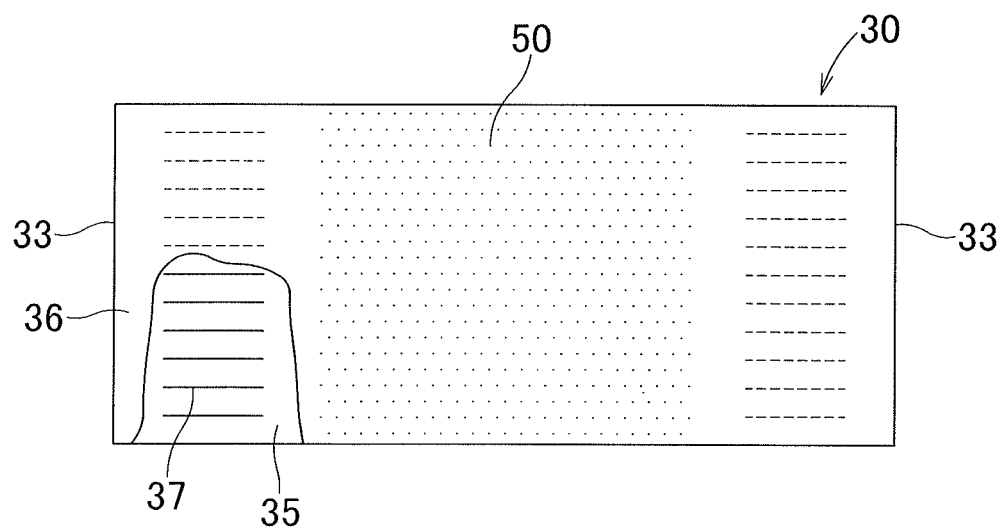
FIG. 12 is a partially cutaway diagram of the skin-contactable sheet.

FIG. 10 illustrates the pad 1 according to a third embodiment. FIG. 11 is a sectional view taken along line XI-XI in FIG. 10 and FIG. 12 is a diagram illustrating the skin-contactable sheet 30. The pad 1 according to this third embodiment is characterized in that the chassis 10 further includes a pair of leakage-barrier cuffs 40 attached to the skin-facing side of the chassis 10. The components similar to those in the first embodiment are denoted by reference signs similar to those in the first embodiment and details thereof will not repetitively described.

The pair of leakage-barrier cuffs 40 are attached to lateral portions of the chassis 10. The pair of leakage-barrier cuffs 40 are spaced apart from each other in the transverse direction and extend between the front end 14 and the rear end 15. Along the front and rear ends 14, 15, the front lateral portions 16a, the rear lateral portions 16b and the crotch lateral portions 16c, the leakage-barrier cuffs 40 are bonded to the inner sheet 17 by bonding means 41 such as hot melt adhesives so as to form respective bonded regions 42. In the regions other than the bonded regions 42, the leakage-barrier cuffs 40 are not bonded to the inner sheet 17 to define respective free regions 43 which may be spaced from the inner sheet 17.

The leakage-barrier cuffs 40 are provided along the inner edges of the respective free regions 43 along distal edges with cuff elastic elements 44 extending in the longitudinal direction Y. The cuff elastic elements 44 are attached under tension and contractibly in the longitudinal direction Y to the respective leakage-barrier cuffs. Upon contraction of these cuff elastic elements 44, the free regions 43 are spaced away from the inner sheet 17 toward the thighs of the wearer to prevent leakage of body waste such as urine.

The skin-contactable sheet 30 is interposed between the above-mentioned leakage-barrier cuffs 40 and the inner sheet 17. The skin-contactable sheet 30 has the first sheet 35 lying on the side of the leakage-barrier cuffs 40, the second sheet 36 lying on the side of the inner sheet 17 and the plurality of elastic elements 37 interposed between these first and second sheets 35, 36. FIG. 12 is a plan view illustrating the elastic elements 37 in a stretched state as viewed from the side of the second sheet 36.

The elastic elements 37 are attached to the skin-contactable sheet 30 in the regions thereof overlapping the respective leakage-barrier cuffs 40. The elastic elements 37 are contractibly attached thereto under tension so as to extend in the transverse direction X and to be spaced apart from each other in the longitudinal direction Y. In this regard, none of the elastic elements 37 is attached thereto in vicinities of the lateral portions 33. Consequently, the skin-contactable sheet 30 is formed in the regions in which the elastic elements 37 are present with the ridges 38 extending in the longitudinal direction Y and the grooves 39 between each pair of the adjacent ridges 38. Specifically, a midsection in the transverse direction X and the lateral portions 33 of the skin-contactable sheet 30 are free from the contractile force of the elastic elements 37 and maintained in a flat state. The skin-contactable sheet 30 is bonded to the inner sheet 17 by the bonding means 34 in a contracted state. The bonding means 34 are formed along the lateral portions remaining in a flat state. The elastic elements 37 may be similar to those used in the second embodiment.

By attaching the elastic elements 37 to the skin-contactable sheet in the manner as has been described above, it is possible to make the skin-contactable sheet 30 partially elastically contractible in the transverse direction X and thereby enlarge a range in which the skin-contactable sheet 30 may move relative to the inner sheet 17.

The second sheet 36 of the skin-contactable sheet 30 is coated on the side facing the inner sheet 17 with a silicon resin serving as friction resistance alleviating means 50. The friction resistance alleviating means 50 is formed in the flat region defined between two sets of the elastic elements 37. The friction resistance alleviating means 50 formed in this manner functions to alleviate the friction between the skin-contactable sheet and the inner sheet 17 and thereby ensure that the skin-contactable sheet 30 may further smoothly move relative to the inner sheet 17.

When lubricant material cosmetically acceptable, for example, silicon resin is used as the friction resistance alleviating means 50, the skin-contactable sheet 30 may be coated with the silicon resin in an intermittent pattern. For example, a plurality of silicon resin lines extending in the longitudinal direction Y and spaced apart from each other in the transverse direction may be formed as the friction resistance alleviating means 50. Alternatively, a film such as a plastic film having a low friction coefficient may be laminated as the friction resistance alleviating means 50 on the second sheet 36. As such a plastic film, at least a film formed of polyethylene or polypropylene may be used.

While the friction resistance alleviating means 50 is formed on the side of the skin-contactable sheet 30 according to this embodiment, the friction resistance alleviating means 50 may be formed on the side of the inner sheet 17 facing this skin-contactable sheet 30, with use of the silicon resin coating or the plastic film laminating.

The leakage-barrier cuffs 40 are spaced apart from each other in the transverse direction X and the skin-contactable sheet 30 is exposed between them so that the skin-contactable sheet 30 may be put in contact with the wearer's body. Such an exposed region of the skin-contactable sheet 30 is not provided with the elastic elements 37 and neither the ridges 38 nor the grooves 39 are formed in this region. Consequently, it is possible to prevent compression traces due to these ridges 38 and the grooves 39 from being left on the wearer's skin and, in addition, undesirable skin irritation may be alleviated.

While the skin-contactable sheet 30 is interposed between the leakage-barrier cuffs 40 and the inner sheet 17 according to this embodiment, the skin-contactable sheet 30 may be attached on the skin-facing side of the leakage-barrier cuffs 40, so that movements of the skin-contactable sheet 30 may be more smooth.

<Fourth Embodiment>

Figure 13:
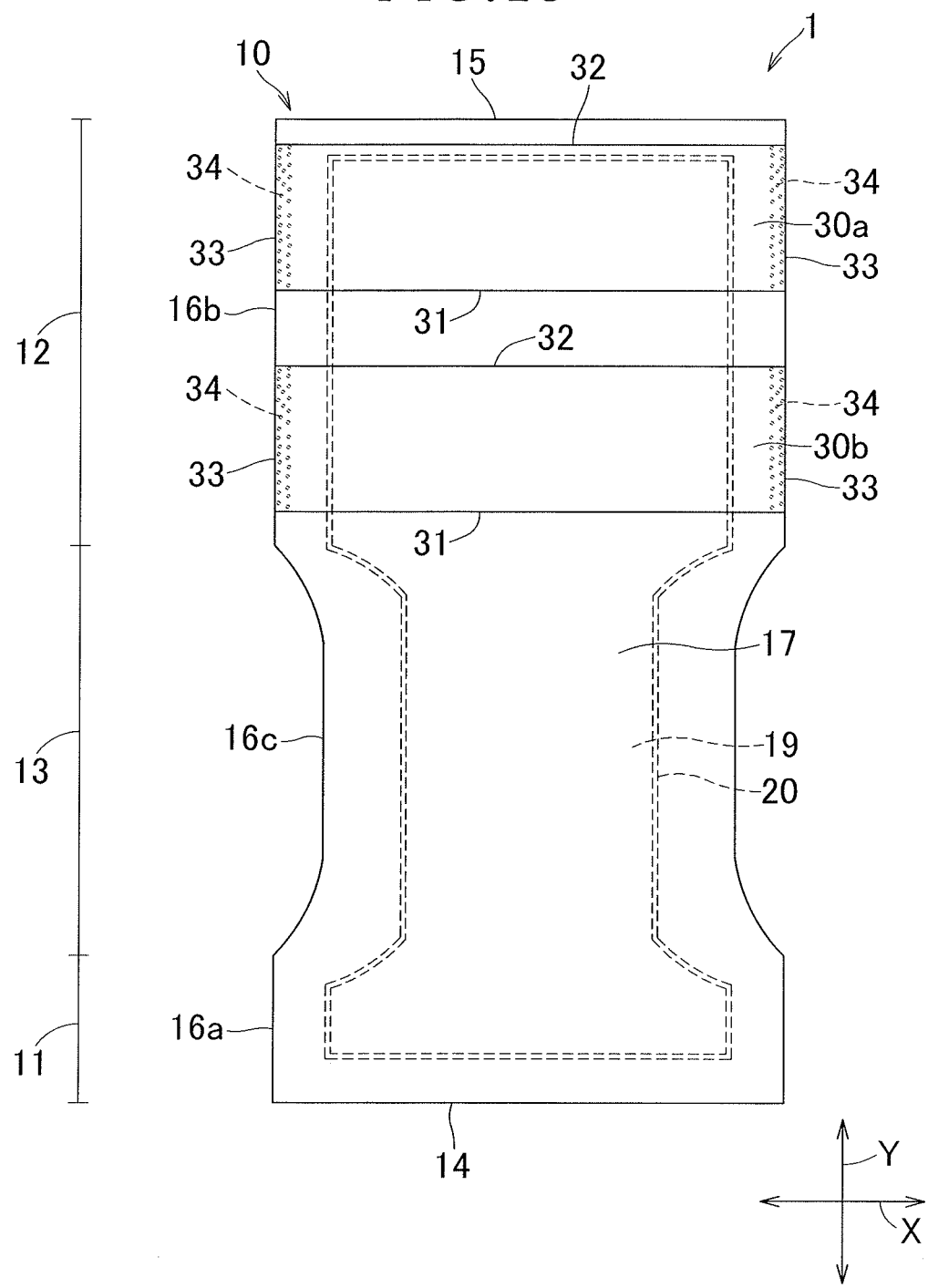
FIG. 13 is a plan view of the pad according to a fourth embodiment.

FIG. 13 illustrates the pad 1 according to a fourth embodiment. This embodiment is characterized in that two or more skin-contactable sheets are attached to the pad 1 and the other components are similar to those in the first embodiment. These similar components are denoted by the reference signs similar to those in the first embodiment and details thereof will be not repetitively described.

On the skin-facing side of the chassis 10, the rear waist region 12 is provided with a pair of skin-contactable sheets 30a, 30b spaced apart from each other in the longitudinal direction Y wherein the skin-contactable sheet 30a is located closer to the rear end 15 and the skin-contactable sheet 30b is located closer to the crotch region 13. Both the skin-contactable sheet 30a and the skin-contactable sheet 30b are bonded to the inner sheet 17 by the bonding means 34 formed only along the respective lateral portions 33. Preferably, the skin-contactable sheet 30a is located so as to cover the wearer's sacral bone region and the skin-contactable sheet 30b is located so as to cover the wearer's ischial bone.

By providing two skin-contactable sheets in the manner as described above, not only the skin-contactable sheets can be put in contact with the wearer's body over a correspondingly larger area but also undesirable friction between the pad 1 and the wearer's skin may be more effectively prevented because these two skin-contactable sheets may separately move relative to the inner sheet 17. Particularly, the skin-contactable sheet 30a is located to cover the sacral bone region which is prominent from the rest and the skin-contactable sheet 30b is located to cover the ischial bone region on which the wearer's body weight is apt to get centered when the wearer sits down. Considering that these sacral bone region and ischial bone region are prone to develop the bedsores, the skin-contactable sheets 30a, 30b are effective to prevent it.

While two skin-contactable sheets 30a, 30b are used in this embodiment, the number of the skin-contactable sheets is not limited to two but three or more skin-contactable sheets may be used. Depending on the number of the skin-contactable sheets or the size of the respective skin-contactable sheets, these skin-contactable sheets may be arranged so as to be in contact with each other without being spaced from each other. In this regard, the skin-contactable sheets are preferably spaced apart from each other in the longitudinal direction Y so that the space defined between the adjacent skin-contactable sheets may be aligned with the defecation point. In this way, it is possible to prevent feces from staying on at least one of the skin-contactable sheets and to prevent feces from clinging to the wearer's skin.

<Fifth Embodiment>

Figure 14:
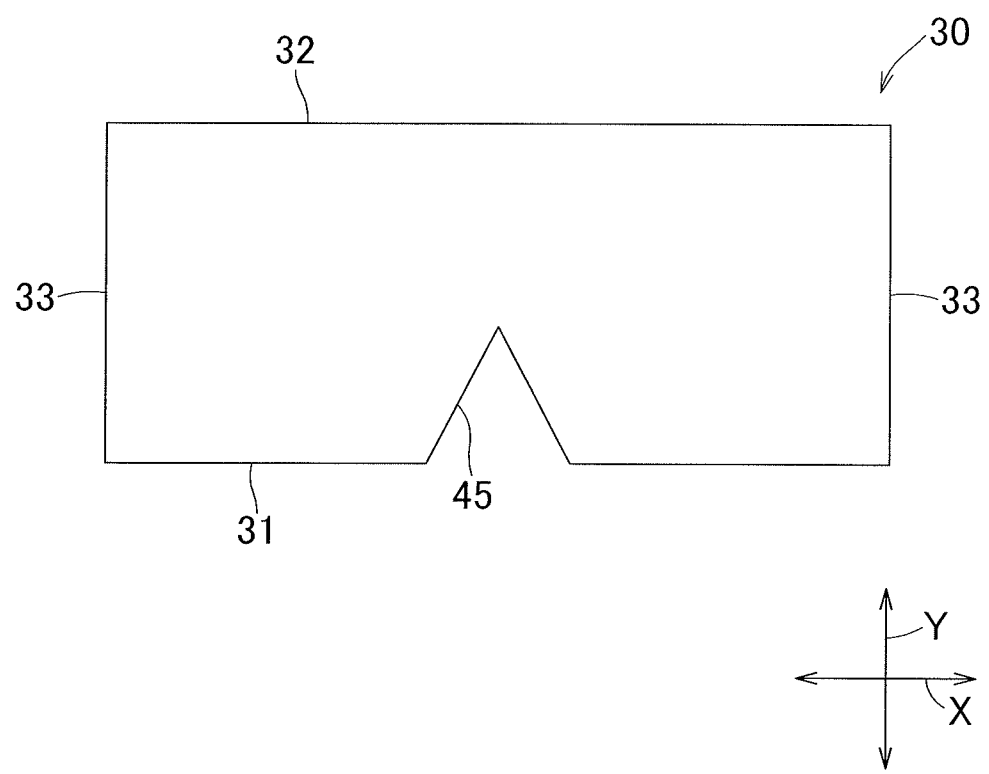
FIG. 14 is a plan view of the skin-contactable sheet according to a fifth embodiment.

FIG. 14 is a diagram illustrating the skin-contactable sheet 30 of the pad according to a fifth embodiment. Description will be limited hereunder to the skin-contactable sheet 30 and other components will be not described.

The front end 31 of the skin-contactable sheet 30 is partially cutout to define a notch region 45. The notch region 45 is formed substantially middle in the transverse direction X and shaped in V opening toward the front end 31. The pad 1 is preferably put on the wearer's body so that the notch region 45 may be aligned with the defecation point of the wearer.

In the pad having such skin-contactable sheet 30, the notch region 45 is aligned with the defecation point and therefore it is not apprehended that at least a portion of feces might stay on the skin-contactable sheet 30 and it is possible to prevent the feces from clinging to the wearer's skin. In addition, formation of the notch region makes it possible to enlarge the dimension of the skin-contactable sheet 30 in the longitudinal direction Y and thereby to put the skin-contactable sheet 30 in contact with the wearer's body over a correspondingly enlarged area.

Sixth Embodiment

Figure 15:
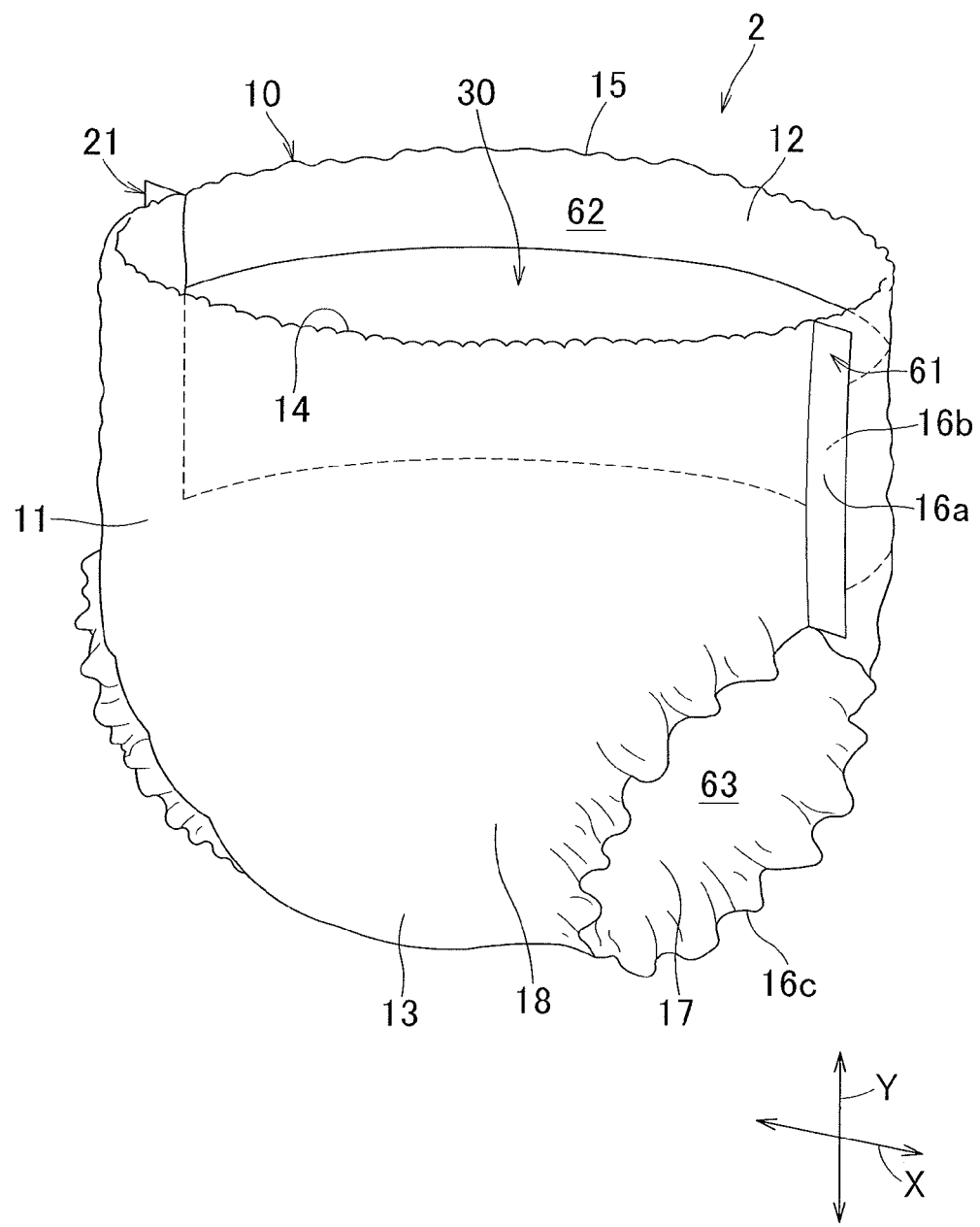
FIG. 15 is a perspective view of a disposable diaper as an example of the disposable wearing article according to a sixth embodiment.
Figure 16:
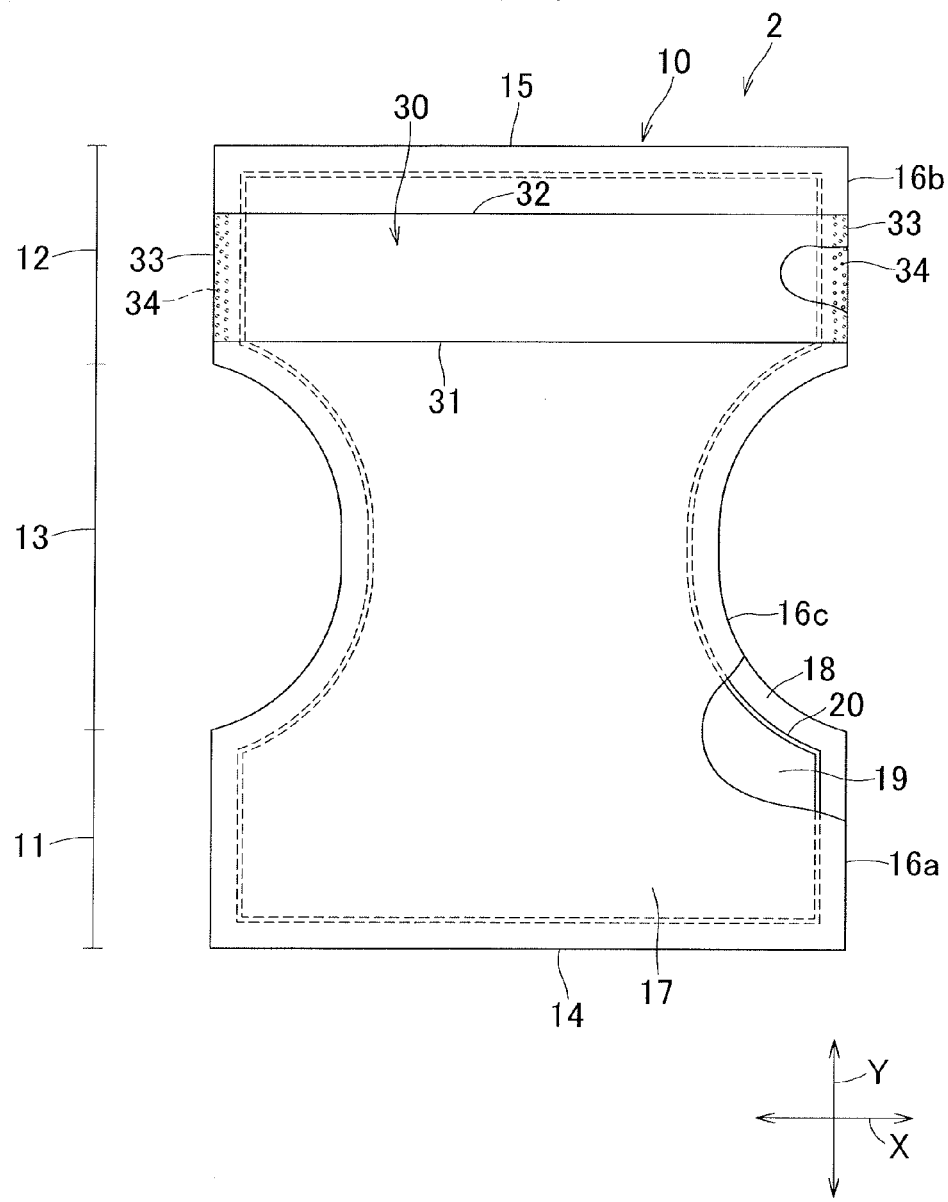
FIG. 16 is a partially cutaway developed plan view of the diaper.

FIGS. 15 and 16 illustrate a disposable diaper 2 according to a sixth embodiment, as another example of the wearing article. FIG. 15 is a perspective view of the diaper 2 having a waist-opening kept in an annular state and FIG. 16 is a plan view of the diaper 2 flatly developed state. The components similar to those in the pad 1 according to the first embodiment are denoted by the reference signs similar to those in the first embodiment and details thereof will be not described hereunder.

The front waist region's lateral portions 16a and the rear waist region's lateral portions 16b are bonded to each other to define seams 61. By forming the seams 61, a waist-opening 62 and leg-openings 63 are formed. In the diaper 2, the crotch region 13 is located about the imaginary transverse center line Q-Q and a dimension of the front waist region 11 in the longitudinal direction and a dimension of the rear waist region 12 in the longitudinal direction are substantially the same.

In the diaper 1 constructed as has been described above, the skin-contactable sheet 3 is located in the rear waist region 12 on the side of the chassis 10 facing the wearer's body. Specifically, the skin-contactable sheet 30 is bonded to the inner sheet 17 by the bonding means 34 in the rear waist region 12. The bonding means 34 are provided only the lateral portions 33 of the skin-contactable sheet 30 and, between the opposed bonding means 34, the skin-contactable sheet 30 is not bonded to the inner sheet 12. In consequence, in the free region defined between the opposite bonding means 34, the skin-contactable sheet 30 can move relative to the inner sheet 17. Such a skin-contactable sheet 30 may be made elastically contractible at least in the transverse direction X.

While a pull-on type diaper of which the front waist region's lateral portions 16a and the rear waist region's lateral portions 16b are previously joined together is exemplarily described in this embodiment, this invention is applicable also to open-type diapers of which the front waist region's lateral portions 16a and the rear waist region's lateral portions 16b are not previously joined together.

While the disposable wearing article in which the crotch region 13 having the dimension in the transverse direction X dimensioned to be smaller than those of the front and rear waist region has been described hereinbefore, a substantially rectangular wearing article in which the dimension in the transverse direction X is substantially uniform in the front waist region 11, the rear waist region 12 and the crotch region 13 is not excluded from this invention. In such a rectangular wearing article, the portion adapted to lie in the wearer's crotch may be defined as the crotch region 13, the portion adapted to lie on the wearer's ventral side extending forward may be defined as the front waist region 11 and the portion adapted to lie on the dorsal side extending rearward from the crotch region 13 may be defined as the rear waist region 12. In this case, the skin-contactable sheet 30 is preferably located closer to the side of the rear end than the imaginary transverse center line Q-Q.

The constituent members of the pad 1 and the diaper 2 are not limited to those described in the specification but the other various types of known materials widely used in the relevant technical field may be used without limitation.

In the above described embodiments, one of these embodiments may be added with or combined with the element and the construction of any other embodiment. For example, the friction resistance alleviating means 50 used in the second embodiment may be applied to the other embodiments.

{Reference Signs List}
1 disposable urine absorbent pad (disposable wearing article)
2 diaper (disposable wearing article)
10 chassis
11 front waist region
12 rear waist region
13 crotch region
14 front end
15 rear end
16a front lateral portions
16b rear lateral portions
16c crotch lateral portions
30 skin-contactable sheet
31 front end
32 rear end
33 lateral portions
38 ridges
39 grooves
40 leakage-barrier cuffs
42 bonded regions
43 free regions
45 notch region
50 friction resistance alleviating means

The invention claimed is:

1. A disposable wearing article having a longitudinal direction and a transverse direction, said disposable wearing article including:
   a chassis including
      a skin-facing side, a non-skin-facing side opposite to the skin-facing side,
      a front waist region, a rear waist region and a crotch region extending between the front and rear waist regions,
      lateral portions extending in the longitudinal direction, and
      front and rear ends extending in the transverse direction; and
   a skin-contactable sheet lying on the skin-facing side of the chassis,
   wherein
   the skin-contactable sheet extends in the transverse direction, lies at least in the rear waist region and is joined to the chassis only along lateral portions of the skin-contactable sheet,
   the skin-contactable sheet further includes:
      a plurality of elastic elements contractibly attached to the skin-contactable sheet; and
      a plurality of ridges extending in the longitudinal direction and grooves each formed between a pair of the adjacent ridges,
   wherein a middle section of the skin-contactable sheet in the transverse direction is free from the contractile force of the plurality of elastic elements and is in a flat state without the ridges and grooves.

2. The disposable wearing article defined by claim 1, wherein the skin-contactable sheet is elastically contractible at least in the transverse direction.

3. The disposable wearing article defined by claim 1, wherein the skin-contactable sheet has front and rear ends extending in the transverse direction and a notch region defined by partially cutting out the front end.

4. The disposable wearing article defined by claim 1, further comprising:
a further skin-contactable sheet,
wherein
the further skin-contactable sheet and the skin-contactable sheet are arranged next to each other in the longitudinal direction,
the further skin-contactable sheet extends in the transverse direction and is joined to the chassis only along lateral portions of the further skin-contactable sheet,
the further skin-contactable sheet further includes:
a plurality of further elastic elements contractibly attached to the further skin-contactable sheet; and
a plurality of further ridges extending in the longitudinal direction and further grooves each formed between a pair of the adjacent further ridges, and
a middle section of the further skin-contactable sheet in the transverse direction is free from the contractile force of the plurality of further elastic elements and is in a flat state without the further ridges and further grooves.

5. The disposable wearing article defined by claim 1, further comprising a resistance alleviating member applied, in an overlapping region of the skin-contactable sheet and the chassis, on at least one of a side of the skin-contactable sheet facing the chassis and a side of the chassis facing the skin-contactable sheet.

6. The disposable wearing article defined by claim , wherein the friction resistance alleviating member comprises lubricant material.

7. The disposable wearing article defined by claim 6, wherein the lubricant material is a silicon resin.

8. The disposable wearing article defined by claim 1, wherein a dimension of the crotch region in the transverse direction is smaller than those of the front and rear waist regions.

9. The disposable wearing article defined by claim 1, wherein a dimension of the rear waist region in the longitudinal direction is larger than that of the front waist region.

10. The disposable wearing article defined by claim 1, wherein
the chassis is formed on the skin-facing side with a pair of leakage-barrier cuffs including:
bonded regions extending along the lateral portions of the wearing article in the longitudinal direction and bonded to the chassis; and
free regions not bonded to the chassis and adapted to be spaced therefrom,
wherein the skin-contactable sheet is attached to the chassis so as to at least partially overlap with the leakage-barrier cuffs.

11. The disposable wearing article defined by claim 10, wherein the skin-contactable sheet is attached to be interposed between the leakage-barrier cuffs and the chassis.

12. The disposable wearing article defined by claim 10, wherein the skin-contactable sheet is elastically stretchable and contractible in the transverse direction in a region of the skin-contactable sheet overlapping the leakage-barrier cuffs.

13. The disposable wearing article defined by claim 10, wherein the ridges and grooves are only formed in regions below the leakage-barrier cuffs in the thickness direction.

14. The disposable wearing article defined by claim 4, wherein
a dimension of the crotch region in the transverse direction is smaller than those of the front and rear waist regions,
the further skin-contactable sheet and the skin-contactable sheet are spaced from each other in the longitudinal direction, and
both the further skin-contactable sheet and the skin-contactable sheet are arranged in the rear waist region.

* * * * *